United States Patent
Nomura et al.

[11] Patent Number: 5,891,124
[45] Date of Patent: Apr. 6, 1999

[54] DISPOSABLE TRAINING PANTS

[75] Inventors: Hironori Nomura, Iyomishima; Tohru Sasaki; Toshifumi Ohtsubo, both of Kawanoe, all of Japan

[73] Assignee: Uni-Charm Corporation, Ehime-ken, Japan

[21] Appl. No.: 780,011

[22] Filed: Dec. 23, 1996

Related U.S. Application Data

[63] Continuation of Ser. No. 343,937, Nov. 17, 1994, abandoned.

[30] Foreign Application Priority Data

Nov. 26, 1993 [JP] Japan .................................. 5-063525

[51] Int. Cl.[6] ..................................................... A61F 13/15
[52] U.S. Cl. ........................................ 604/385.1; 604/392
[58] Field of Search ..................................... 604/358, 369, 604/373, 378, 385.1, 385.2, 392, 394, 396

[56] References Cited

U.S. PATENT DOCUMENTS

| | | | |
|---|---|---|---|
| 4,891,258 | 1/1990 | Fahrenkrug | 604/385.1 |
| 4,895,568 | 1/1990 | Enloe | 604/385.1 |
| 5,342,343 | 8/1994 | Kitaoka et al. | 604/385.1 |
| 5,425,726 | 6/1995 | Shimizu et al. | 604/385.1 |
| 5,527,300 | 6/1996 | Sauer | 604/385.1 |

FOREIGN PATENT DOCUMENTS

| | | |
|---|---|---|
| 5-19305 | 3/1993 | Japan . |
| 5-59601 | 3/1993 | Japan . |

*Primary Examiner*—John G. Weiss
*Assistant Examiner*—David J. Cho
*Attorney, Agent, or Firm*—Lowe Hauptman Gopstein Gilman & Berner

[57] ABSTRACT

Disposable training pants comprising a stretchable moisture holding sheet which is bonded at its longitudinally opposite ends to the top surface of a topsheet on front and rear bodies as the moisture holding sheet is stretched in longitudinally opposite directions with respect to a crotch zone across said front and rear bodies.

10 Claims, 5 Drawing Sheets

DISPOSABLE TRAINING PANTS

This application is a continuation of application Ser. No. 08/343,937 filed Nov. 17, 1994 now abandoned.

BACKGROUND OF THE INVENTION

The present invention relates to disposable training pants used for training a baby so that any kind of diaper may become unnecessary for the baby as soon as possible.

Various disposable training pants are well known, for example, from Japanese Laid-Open patent application No. 1993-59601 and Japanese Laid-Open utility model application No. 1993-19305. Each of these techniques is based on disposable training pants comprising a liquid-permeable topsheet, a liquid-impermeable backsheet, a liquid-absorbent core sandwiched between these two sheets, and a waist-opening and a pair of leg-openings both provided therearound with stretchable elastic members, respectively. According to the technique disclosed in said patent application No. 1993-59601, a moisture holding sheet is bonded to the top surface of the topsheet so that the moisture holding sheet may be partially floated up and, according to the technique disclosed in said utility model application No. 1993-19305, a moisture holding sheet is adhesively laminated on the top surface of the topsheet. Both these two techniques are characterized in that the moisture holding sheet is normally kept in contact with the wearer's crotch zone to make the wearer feel wet when the excretion of urine occurs and the moisture holding sheet is wetted therewith, and suitable spongy material is used to form the moisture holding sheet in order that the wearer can not be prevented from feeling wet so far as the training pants put on the wearer's body slip down only by a predetermined slight dimension during the movement of the wearer's body. Particularly according to said patent application No. 1993-59601, the moisture holding sheet is partially floated up and thereby said dimension by which the pants may slid down is substantially compensated.

However, both said techniques have been confronted with a problem that it will be no more possible to make the wearer feel wet if the pants slip down by a dimension larger than the thickness or the floating up of the moisture holding sheet. If it is attempted to solve such problem by increasing the thickness or the floating up of the moisture holding sheet, not only a comfortable wearing feel will be impaired even if the pants are normally put on the wearer's body but also the wastefully increased material should be used to assemble the pants. Thus, such solution is meaningless.

It is a principal object of the invention to solve the above-mentioned problem of said well known techniques by stretching a stretchable moisture holding sheet in longitudinally opposite directions with respect to the crotch zone of the training pants across front and rear bodies and bonding the moisture holding sheet in this stretched condition at its longitudinally opposite ends to the top surface of the topsheet so as to serve as make feel-wet means.

SUMMARY OF THE INVENTION

The object set forth above is achieved, according to the invention, by disposable training pants comprising a liquid-permeable topsheet, a liquid-impermeable backsheet, a liquid-absorbent core sandwiched between these two sheets, and make-feel-wet means provided on the top surface of said topsheet, wherein said make-feel-wet means comprises a stretchable moisture holding sheet having a moisture holding capacity higher than that of said topsheet and bonded at its longitudinally opposite ends by permanent bonding means to said top surface on front and rear bodies, as said stretchable moisture holding sheet is stretched in longitudinally opposite directions with respect to a crotch zone across said front and rear bodies.

In an embodiment of the invention, said moisture holding sheet is bonded along its extent between said longitudinally opposite ends temporary bonding means to said top surface.

With the training pants constructed as has been described above, the stretchable moisture holding means permanently bonded at its longitudinally opposite ends to the front and rear bodies floats up above the crotch zone of the pants on said opposite ends as the pants are put on the wearer's body. The floating up of the moisture holding sheet allows it to be maintained in contact with the crotch zone of the wearer even if the pants slid down by a considerable dimension. This moisture holding sheet can make the wearer feel wet when the sheet is wetted with liquid excretion.

The moisture holding sheet temporarily bonded along its extent between said longitudinally opposite ends is separated and floated up from the topsheet only when the excretion of urine occurs.

BRIEF DESCRIPTION OF THE DRAWINGS

The invention will be described by way of example in reference with the accompanying drawing, in which.

PREFERRED EMBODIMENTS OF THE INVENTION

Figure 1:
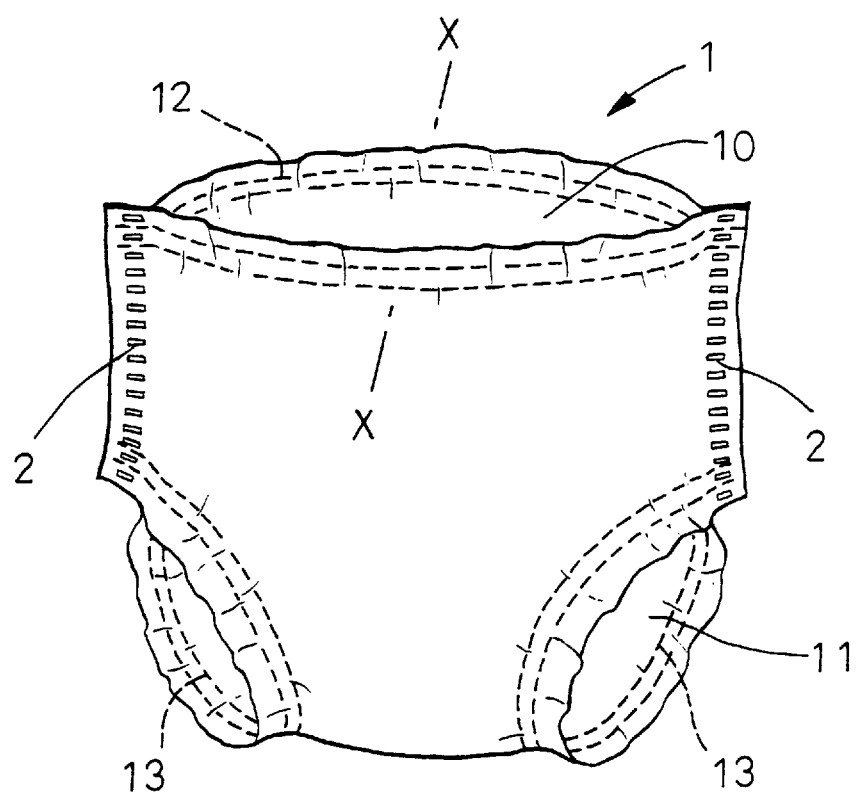
FIG. 1 is a perspective view showing training pants according to the invention.

Referring to FIG. 1, training pants 1 is perspectively shown as put on the wearer's body.

Figure 2:
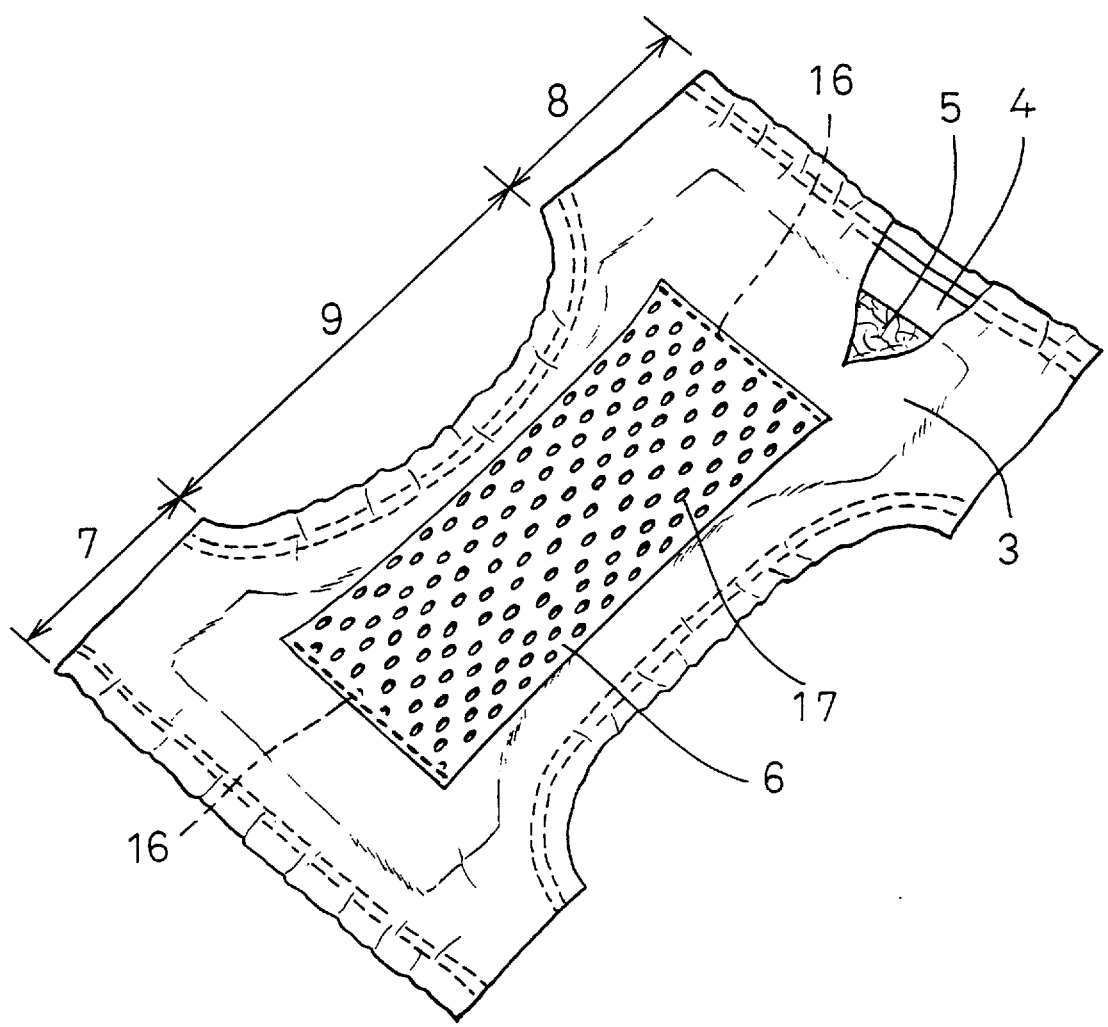
FIG. 2 is a developed perspective view of the training pants.

Referring to FIG. 2, the pants of FIG. 1 is perspectively shown as front and rear bodies have been separated from each other along transversely opposite bonding lines adjacent the waist line and then longitudinally developed.

Referring to FIGS. 1 and 2, the pants 1 comprise a liquid-permeable topsheet 3, a liquid-impermeable backsheet 4, a liquid-absorbent core 5 sandwiched between these two sheets 3, 4, and a moisture holding sheet 6 bonded to the central zone on the top surface of the topsheet 3, wherein said top- and backsheets 3, 4 are substantially identical in their configurations and intermittently bonded to each other over their portions extending outwards from the peripheral edge of the core 5. The pants 1 have front and rear bodies 7, 8 and a crotch zone 9 interposed between these front and rear bodies 7, 8. From the developed state as seen in FIG. 2, a blank of the pants 1 may be folded in two with the topsheet 3 lying inside and then the front and rear bodies may bonded to each other along their mutually facing side edges to complete the pants 1 having a waist-opening 10 and a pair of leg-openings 11 as shown by FIG. 1. Elastic members 12, 13 are bonded in their stretched condition to peripheral edges of the respective openings.

Referring to FIG. 2, the moisture holding sheet 6 is a stretchable rectangular strip of spongy sheet such as foamed urethane which is formed smaller than the topsheet 3 and bonded at its longitudinally opposite ends by permanent bonding means 16 to the top surface of the topsheet 3 on the front and rear bodies 7, 8, respectively, as said moisture holding sheet 6 is stretched in longitudinally opposite directions with respect to the crotch zone 9 across said front and rear bodies 7, 8. The sheet 6 is provided with perforations 17 facilitating liquid excretion to be transferred to the topsheet 3.

Figure 3:
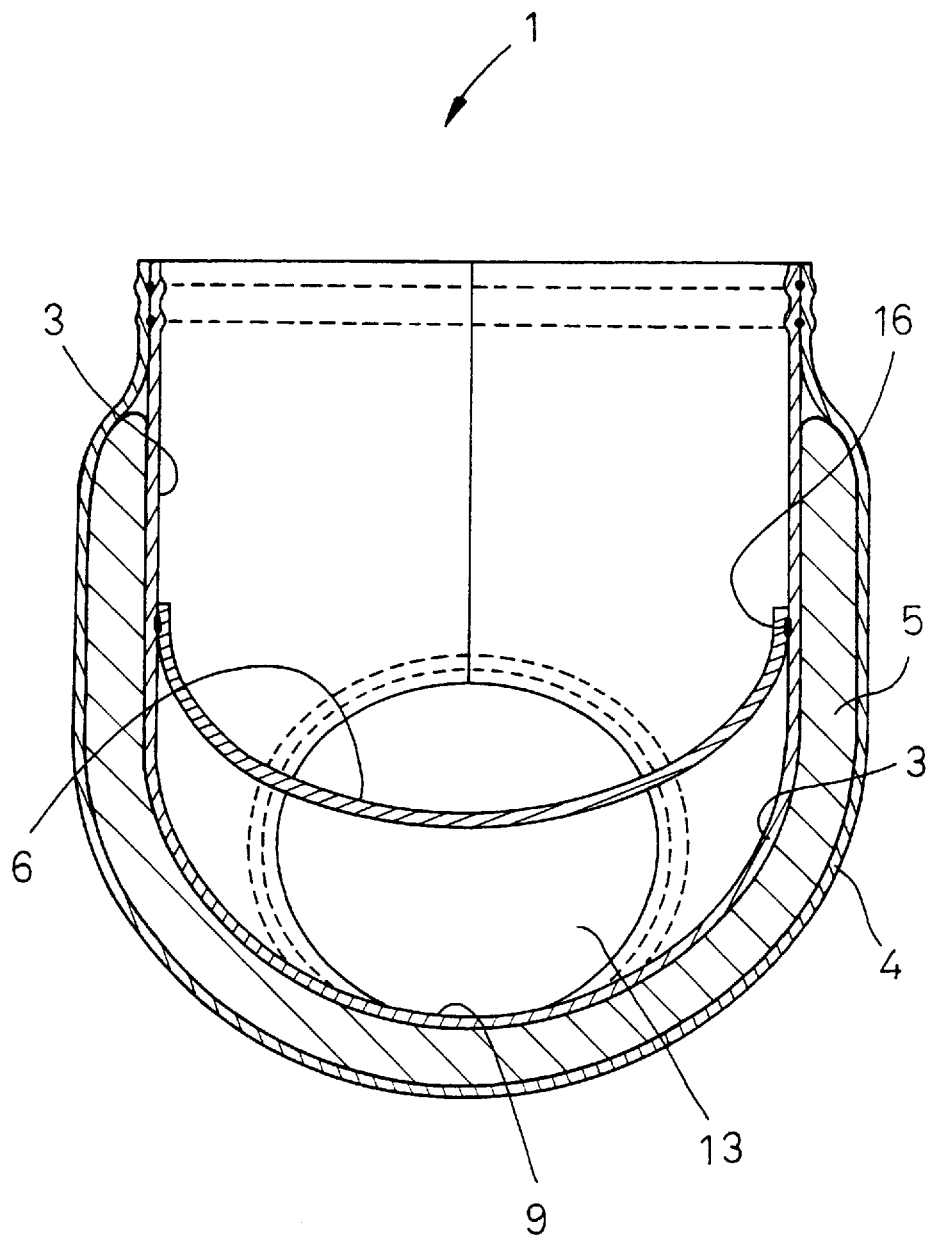
FIG. 3 is a sectional view taken along a line X—X in FIG. 1.

FIG. 3 is a sectional view taken along a line X—X in FIG. 1. With the pants 1 put on the wearer's body, the moisture holding sheet 6 elastically contracts between the opposite ends at which the moisture holding sheet 6 has been bonded to the topsheet 3 and tends to float up at the crotch zone 9 from the topsheet 3. The dimension of such floating up adjustably depends on factors such as the positions at which the moisture holding sheet 6 is bonded to the topsheet 3 and the elongation percentage of the moisture holding sheet 6. Such moisture holding sheet 6 can be maintained in contact with the crotch zone of the wearer's body even if the pants 1 once put on the wearer's body slip down to some degree, and therefore can reliably make the wearer feel wet when the moisture holding sheet 6 is wetted with liquid excretion.

Figure 4:
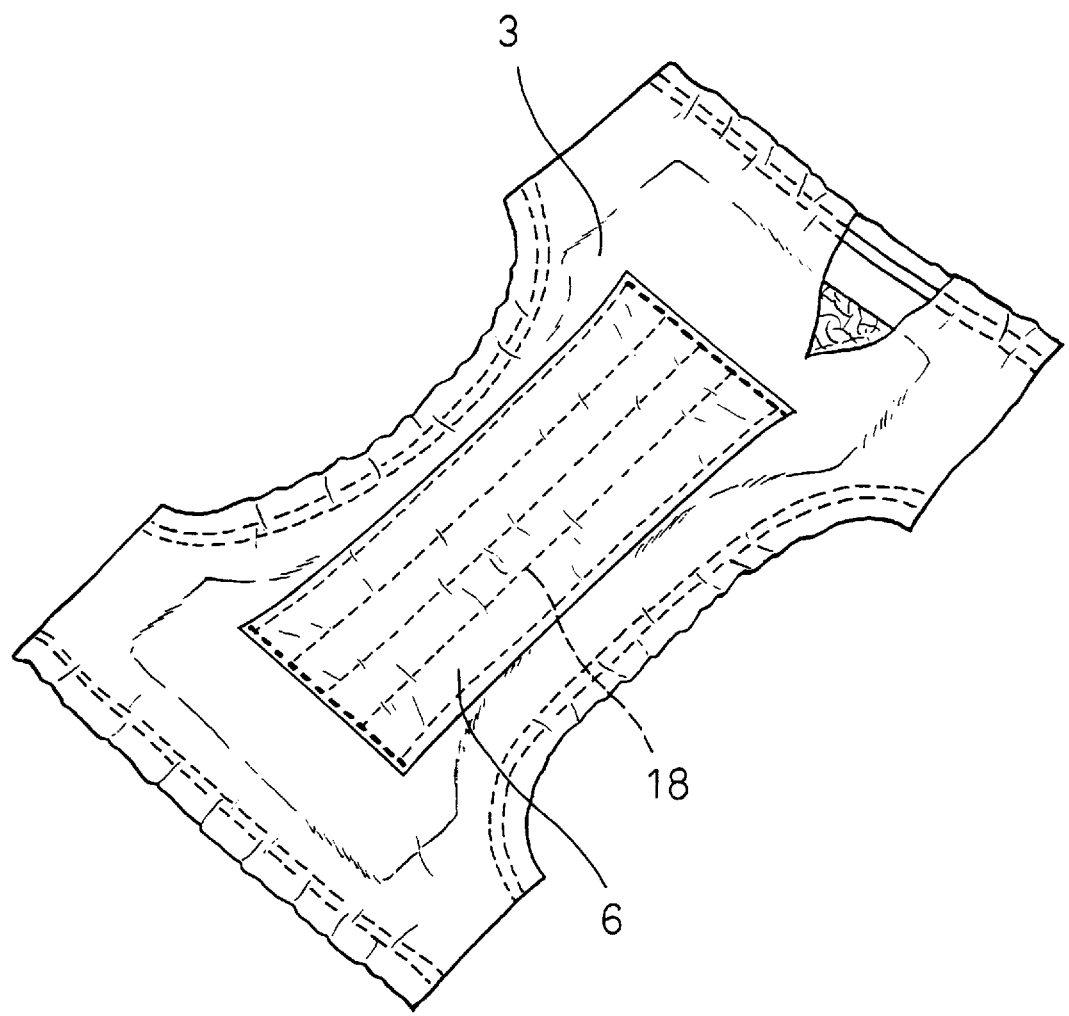
FIG. 4 is a perspective view similar to FIG. 2 exemplary showing an embodiment of the moisture holding sheet.

FIG. 4 is a view similar to FIG. 2, exemplary showing another embodiment of the moisture holding sheet 6. As shown, a plurality of rubber threads 18 are adhesively bonded in their stretched condition to the lower surface of the moisture holding sheet 6 comprising a rectangular strip made of a non-stretchable nonwoven fabric and this sheet 6 is bonded in its stretched condition to the top surface of the topsheet 3 at its longitudinally opposite ends. With the pants 1 being put on the wearer's body, said nonwoven fabric constituting the sheet 6 is finely wrinkled under the contraction of the rubber threads 18 and tends to float up from the topsheet 3 as in the case shown by FIG. 3.

Figure 5:
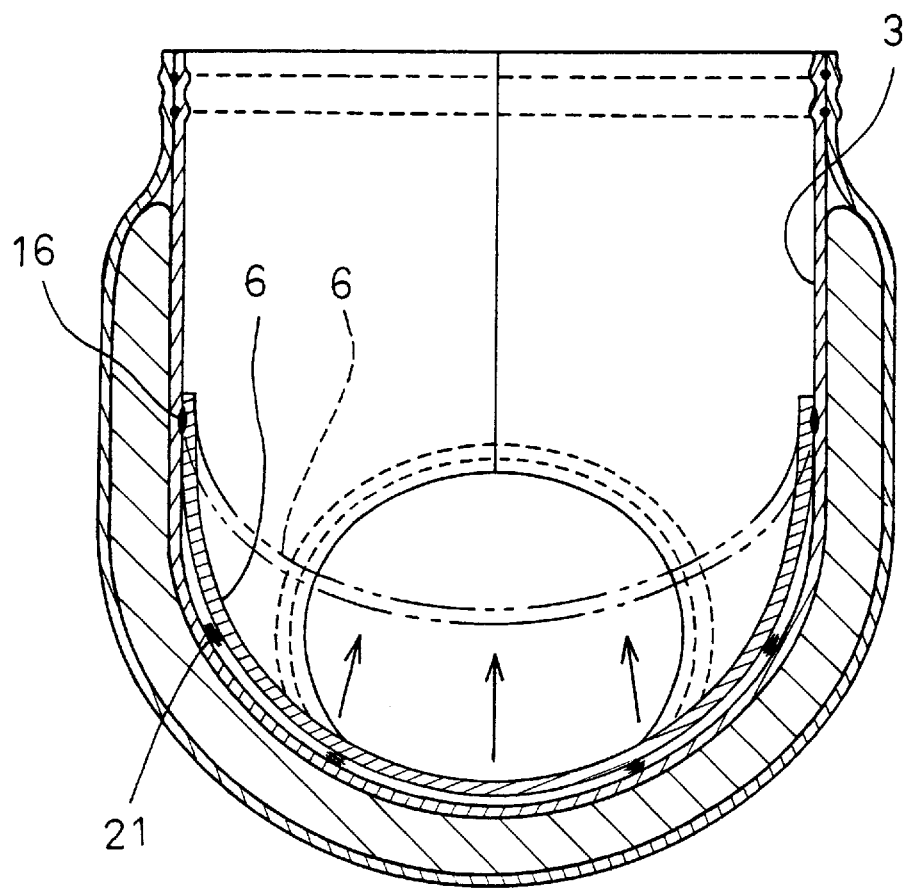
FIG. 5 is a sectional view similar to FIG. 3 showing the training pants employing another embodiment of the moisture holding sheet.

FIG. 5 is a view similar to FIG. 3, showing further another embodiment of the moisture holding sheet 6. As shown, the moisture holding sheet 6 is bonded by temporary bonding means 21 over its extent defined between the longitudinally opposite ends bonded by the permanent bonding means 16 to the top surface of the topsheet intermittently on the top surface of the topsheet 3 so that liquid excretion may reduce an anchoring effect by said water-soluble adhesive 21 and, in consequence, the moisture holding sheet 6 may contract away from the topsheet 3 in the direction as indicated by an arrow into a position indicated by an imaginary line. In view of a fact that, while the moisture holding sheet 6 should be maintained in contact with the wearer's skin and thereby reliably make the wearer feel wet, such contact with the wearer's skin prior to the occurrence of urination may obstruct a desired air-permeability around the crotch zone, it is preferred to maintain a good air-permeability at least before the excretion of urine occurs by employing the specific embodiment of the moisture holding sheet 6 shown by FIG. 5.

In the training pants 1, the topsheet 3 may be formed by a nonwoven fabric or woven fabric made of synthetic fibers, natural fibers or a mixture thereof, or by a perforated film made of synthetic resin.

The moisture holding sheet 6 may be formed by a sheet having a moisture holding capacity per unit area higher than that of the topsheet 3. For example, a stretchable sheet such as a soft urethane spongy sheet or polyethylene spongy sheet having an expansion ratio of 20 to 70 and a thickness of 1 to 6mm or a nonwoven fabric sheet made of crimped fibers or the other stretchable fibers having a weight per unit area of 20 to 200g/m$^2$ may be bonded in its stretched condition to the topsheet 3. Alternatively, the elastic member may be bonded in its stretched condition to a non-stretchable sheet such as a woven fabric, nonwoven fabric or tissue paper, as shown by FIG. 4. To compare the moisture holding capacity of the moisture holding sheet 6 with that of the topsheet 3, for example, after sheet samples of 5×5cm have been immersed in artificial urine for 30 seconds and hung down for 60 seconds to swish water off from these samples, an increase in weight may be comparatively determined. The moisture holding capacity of the moisture holding sheet 6 may be controlled by providing it with perforations each having diameter of 1 to 10mm at an area ratio of 5 to 60%, as shown by FIG. 2. If the moisture holding sheet 6 is made from hydrophobic fibers, it is preferred to use such moisture holding sheet 6 after making it hydrophilic. When a stretchable sheet is employed as at least one of the top-and backsheets 3, 4 to obtain the stretchable pants 1, the moisture holding sheet 6 must have an elongation ratio higher than an elongation ratio of the pants proper 1 during the actual use of the pants 1 in order that the sheet 6 may reliably float off above the topsheet 3. For temporarily bonding the moisture holding sheet 6 over its extent defined between its longitudinally opposite ends to the topsheet 3, that is, for example, for the temporary bonding means 21, water-soluble adhesives such as polyvinylalcohol or starch glue may be employed or the sheets 3, 6 laminated together may be subjected to the emboss treatment. For permanently bonding the moisture holding sheet 6 at its opposite ends to the topsheet 3, that is, for the permanent bonding means 16, bonding technique using hot melt adhesives, the other water-insoluble adhesives or heat welding means for heat weldable material may be employed.

The backsheet 4 may be formed by a synthetic resin film such as a polyethylene film and the core 5 may be formed by a product molded from fluff pulps of a mixture of fluff pulps and super-absorbent polymer powders. Preferably, the core 5 is intermittently bonded to at least one of the top- and backsheets 3, 4.

What is claimed is:

1. A disposable training pants comprising:
   a liquid-permeable topsheet, a liquid-impermeable backsheet and a liquid-absorbent core disposed therebetween to define a front body, a rear body and a crotch zone interposed therebetween of said training pants; and
   a stretchable moisture holding sheet having a moisture holding capacity higher than that of said topsheet and fixedly bonded in a stretched condition at longitudinally opposite ends of said holding sheet with a fixed bonding agent to a top surface of said topsheet,
   wherein said moisture holding sheet is attached to the crotch zone intermediate said longitudinally opposite ends by means of a water soluble adhesive, whereby liquid excretions by the wearer dissolve said water soluble adhesive which releases the moisture holding sheet so that it is biased to lift away from the crotch zone to enter into contact with a wearer's skin.

2. The disposable training pants according to claim 1, wherein said moisture holding sheet is bonded to the top surface of said topsheet over an extent defined between the longitudinally opposite ends by a releasable bonding agent.

3. The disposable training pants according to claim 1, wherein said fixed bonding agent is a water-insoluble adhesive.

4. The disposable training pants according to claim 1, wherein said fixed bonding agent is formed by heat welding.

5. The disposable training pants according to claim 2, wherein said releasable bonding agent is a water-soluble adhesive.

6. The disposable training pants according to claim 1, wherein said moisture holding sheet is provided with a plurality of perforations.

7. The disposable training pants according to claim 1, wherein said moisture holding sheet is formed smaller than said topsheet.

8. The disposable training pants according to a claim 1, wherein said moisture holding sheet is formed of a spongy sheet.

9. The disposable training pants according to claim 1, wherein said moisture holding sheet is formed of a non-stretchable nonwoven fabric, said nonwoven fabric being provided with a plurality of rubber threads secured in their stretched condition to said nonwoven fabric.

10. A disposable training pants comprising:

- a liquid-permeable topsheet, a liquid-impermeable backsheet and a liquid-absorbent core disposed therebetween to define a front body, a rear body and a crotch zone interposed therebetween of said training pants; and
- a stretchable moisture holding sheet fixedly bonded at longitudinally opposite ends thereof to a top surface of said topsheet, whereby said moisture holding sheet, when said training pants are worn, is adapted to bridge over a portion of said crotch zone located therebelow so as to be positioned closer to the wearer's crotch than said crotch zone so that when there is a liquid excretion into the training pants, said moisture holding sheet will retain a part of the liquid excretion and by being in contact with a wearer's skin will make the wearer aware of its own excretion, whereby said holding sheet is lifted away from the crotch zone along substantially the entire length of said holding sheet as measured between the bonded longitudinal ends thereof, wherein said moisture holding sheet is attached to the crotch zone intermediate said longitudinally opposite ends by means of a water-soluble adhesive, whereby liquid excretions by the wearer dissolve said water-soluble adhesive which releases the moisture holding sheet so that it is biased to lift away from the crotch zone so as to enter into the aforesaid contact with said wearer's skin.

* * * * *